(12) United States Patent
Ambro

(10) Patent No.: US 10,517,579 B2
(45) Date of Patent: Dec. 31, 2019

(54) SPECIMEN COLLECTION BAG DEPLOYMENT DEVICE

(71) Applicant: A & M Medical, Inc., Greensboro, NC (US)

(72) Inventor: Andrew J. Ambro, Greensboro, NC (US)

(73) Assignee: A & M Medical, Inc., Greensboro, NC (US)

( * ) Notice: Subject to any disclaimer, the term of this patent is extended or adjusted under 35 U.S.C. 154(b) by 0 days.

(21) Appl. No.: 16/270,366

(22) Filed: Feb. 7, 2019

(65) Prior Publication Data

US 2019/0247031 A1 Aug. 15, 2019

Related U.S. Application Data

(60) Provisional application No. 62/628,782, filed on Feb. 9, 2018.

(51) Int. Cl.
*A61B 17/00* (2006.01)
*A61B 17/221* (2006.01)

(52) U.S. Cl.
CPC ...... *A61B 17/00234* (2013.01); *A61B 17/221* (2013.01); *A61B 2017/00287* (2013.01)

(58) Field of Classification Search
CPC .......................................... A61B 2017/00287
See application file for complete search history.

(56) References Cited

U.S. PATENT DOCUMENTS

| 5,037,379 A * | 8/1991 | Clayman .......... | A61B 17/00234 128/849 |
| 5,341,815 A * | 8/1994 | Cofone ............ | A61B 17/00234 128/DIG. 24 |
| 5,354,303 A * | 10/1994 | Spaeth ............. | A61B 17/00234 604/171 |
| 5,480,404 A * | 1/1996 | Kammerer ....... | A61B 17/00234 606/113 |
| 5,971,995 A * | 10/1999 | Rousseau .......... | A61B 17/00234 606/110 |
| 6,383,197 B1 * | 5/2002 | Conlon ............ | A61B 17/00234 600/37 |
| 2005/0267492 A1 * | 12/2005 | Poncet ................. | A61B 17/221 606/114 |

(Continued)

FOREIGN PATENT DOCUMENTS

| EP | 2621347 B1 | 1/2018 |
| WO | 2014/134285 A1 | 9/2014 |

OTHER PUBLICATIONS

Inzii® Retrieval Systems, 2017, 6 pages, Applied Medical Resources Corporation, Rancho Santa Margarita, California, USA.

(Continued)

*Primary Examiner* — Shaun L David
(74) *Attorney, Agent, or Firm* — Kevin E Flynn; Flynn IP Law

(57) ABSTRACT

A collection bag and a bag deployment device for use in collecting an item such as a specimen during surgical procedure. The collection bag and bag deployment device forming an assembly adapted to deliver the collection bag through an access cannula into a surgical cannula. The assembly adapted to strip the collection bag from the distal end of the bag deployment device and cinch a cinch loop to close the open end of the collection bag.

24 Claims, 15 Drawing Sheets

(56) References Cited

U.S. PATENT DOCUMENTS

| | | | | |
|---|---|---|---|---|
| 2007/0088370 A1* | 4/2007 | Kahle | ............... | A61B 17/00234 606/114 |
| 2009/0182292 A1* | 7/2009 | Egle | ................. | A61B 17/00234 604/327 |
| 2011/0184433 A1* | 7/2011 | Parihar | ............ | A61B 17/00234 606/114 |
| 2011/0184436 A1* | 7/2011 | Shelton, IV | ..... | A61B 17/00234 606/114 |
| 2013/0116592 A1* | 5/2013 | Whitfield | ................ | A61B 10/02 600/562 |
| 2015/0289864 A1* | 10/2015 | Holsten | ............ | A61B 17/00234 606/114 |
| 2015/0297204 A1* | 10/2015 | Horton, Jr. | ........ | A61B 17/00234 606/114 |
| 2016/0324515 A1* | 11/2016 | Ravikumar | ....... | A61B 17/00234 |

OTHER PUBLICATIONS

Anchor* Tissue Retrieval System™ by Conmed, 2017, 3 pages, CONMED Corporation, Utica, New York, USA.
Endopouch Retriever®—Disposable Specimen Retrieval Bag System, 2016, 2 pages, Ethicon US, LLC, Cincinnati, Ohio, USA.
Genistrong—Specimen Retrieval Bag—GENICON, Dec. 23, 2017 (capture date by Archive.org), 2 pages, as found at https://web.archive.org/web/20171223113623/http://geniconendo.com:80/products/specimen-retrieval-2/specimen-retrieval/, GENICON, Inc., Winter Park, Florida, USA.
Espiner—A Material Difference in Retrieval Bags, Aug. 2, 2016 (capture date by Archive.org), 4 pages, as found at http://web.archive.org/web/20160802101619/http://globalmedllc.com/affiliates/espiner, Global Medical Partners, Wrentham, Massachusetts, USA.
Strong. Simple. Reliable., 2016 (per footnote 5, the Instructions for Use for ReliaCatch™ were released in 2016) 3 pages, Medtronic, New Haven, Connecticut, USA.
ReliaCatch™ Specimen Retrieval Bag In-service guide, Oct. 2018, 4 pages, Medtronic, Minneapolis, Minnesota, USA.
Specimen Retrieval Bags—A comprehensive portfolio from Medtronic, Jan. 2018, 1 page, Medtronic, Minneapolis, Minnesota, USA.
Kim, Yeonkyung, PCT International Search Report for PCT Application PCT/US2019/017046, dated May 23, 2019, 4 pages, Korean Intellectual Property Office, Daejeon, South Korea.
Kim, Yeonkyung, PCT Written Opinion of the International Searching Authority for PCT Application PCT/US2019/017046, dated May 23, 2019, 11 pages, Korean Intellectual Property Office, Daejeon, South Korea.

* cited by examiner

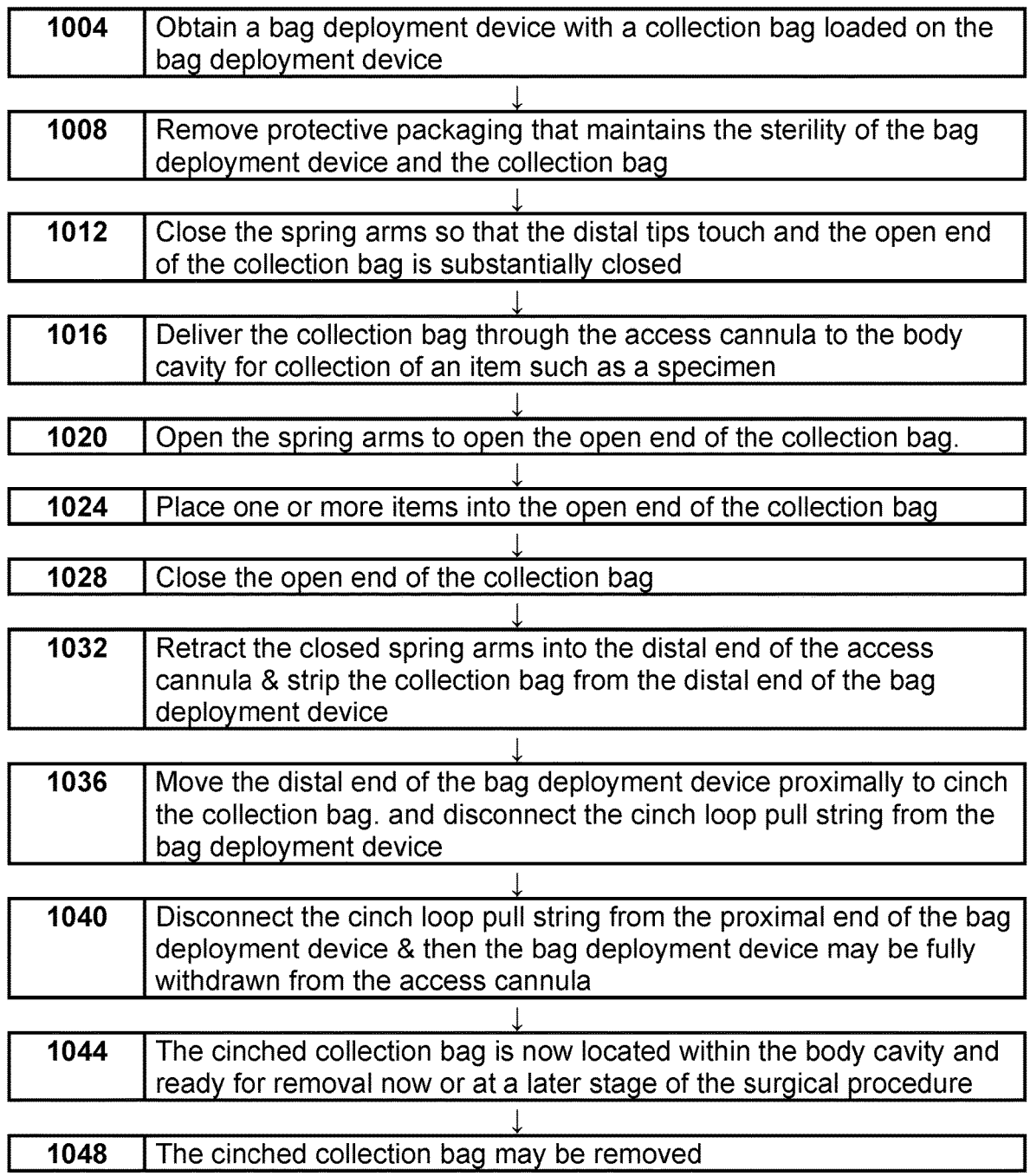

| 1004 | Obtain a bag deployment device with a collection bag loaded on the bag deployment device |
| 1008 | Remove protective packaging that maintains the sterility of the bag deployment device and the collection bag |
| 1012 | Close the spring arms so that the distal tips touch and the open end of the collection bag is substantially closed |
| 1016 | Deliver the collection bag through the access cannula to the body cavity for collection of an item such as a specimen |
| 1020 | Open the spring arms to open the open end of the collection bag. |
| 1024 | Place one or more items into the open end of the collection bag |
| 1028 | Close the open end of the collection bag |
| 1032 | Retract the closed spring arms into the distal end of the access cannula & strip the collection bag from the distal end of the bag deployment device |
| 1036 | Move the distal end of the bag deployment device proximally to cinch the collection bag. and disconnect the cinch loop pull string from the bag deployment device |
| 1040 | Disconnect the cinch loop pull string from the proximal end of the bag deployment device & then the bag deployment device may be fully withdrawn from the access cannula |
| 1044 | The cinched collection bag is now located within the body cavity and ready for removal now or at a later stage of the surgical procedure |
| 1048 | The cinched collection bag may be removed |

SPECIMEN COLLECTION BAG
DEPLOYMENT DEVICE

This application claims the benefit of U.S. Provisional Application No. 62/628,782 filed Feb. 9, 2018 for Specimen Collection Bag Deployment Device. The '782 application is incorporated by reference herein.

BACKGROUND

Field of the Disclosure

This disclosure relates generally to minimally invasive surgical techniques and in particular to specimen retrieval bags and to deployment devices used to manipulate, open, and close the specimen retrieval bags.

Vocabulary.

Unless explicit to the contrary, the word "or" should be interpreted as an inclusive or rather than an exclusive or. Thus, the default meaning of or should be the same as the more awkward and/or.

Proximal and distal should be considered relative to the surgeon. Thus the proximal end of the component is the portion of the component that is towards the end of the device that is not inserted into the patient's body. The distal portion of a component would be the end of the component towards the end of the device that is inserted into the patient's body. In some cases a proximal portion of a component may be further from the inserted end of the device than the surgeon's hand as the surgeon's hand may not always be in contact with the extreme proximal end of the component.

Frequently, when describing an industrial process it is useful to note that a given parameter is substantially met. Examples may be substantially parallel, substantially perpendicular, substantially uniform, substantially closed, and substantially flat. In this context, substantially X means that for purposes of this industrial process it is X. So something that may not be absolutely parallel but is for all practical purposes parallel, is substantially parallel. Likewise, mixed air that has substantially uniform temperature would have temperature deviations that were inconsequential for that industrial process.

As recognized in C. E. Equipment Co. v. United States, 13 U.S.P.Q.2d 1363, 1368 (Cl. Ct. 1989), the word "substantially" in patent claims gives rise to some definitional leeway—thus the word "substantially" may prevent avoidance of infringement by minor changes that do not affect the results sought to be accomplished.

SUMMARY OF THE DISCLOSURE

Aspects of the teachings contained within this disclosure are addressed in the claims submitted with this application upon filing. Rather than adding redundant restatements of the contents of the claims, these claims should be considered incorporated by reference into this summary.

This summary is meant to provide an introduction to the concepts that are disclosed within the specification without being an exhaustive list of the many teachings and variations upon those teachings that are provided in the extended discussion within this disclosure. Thus, the contents of this summary should not be used to limit the scope of the claims that follow.

Inventive concepts are illustrated in a series of examples, some examples showing more than one inventive concept. Individual inventive concepts can be implemented without implementing all details provided in a particular example. It is not necessary to provide examples of every possible combination of the inventive concepts provide below as one of skill in the art will recognize that inventive concepts illustrated in various examples can be combined together in order to address a specific application.

Some aspects of the teachings of the present disclosure may be expressed as an assembly having: a collection bag; and a bag deployment device. The collection bag having: an open end, a closed end opposite the open end with the open end having a drawstring passageway with a cinch loop within the drawstring passageway. The collection bag also having a cinch loop pull string with a distal end that is the cinch loop around a perimeter at the open end of the collection bag and a proximal end that extends out a proximal end of the assembly. The collection bag also having a pair of spring openings to receive distal portions of a pair of spring arms from the bag deployment device.

The bag deployment device having: a first spring arm; a second spring arm; forming the pair of spring arms; and each spring arm having a substantially straight proximal portion, a curved intermediate portion and a distal tip.

The bag deployment device having a drive rod with a distal end of the drive rod connected to the proximal portions of the pair of spring arms and a proximal end of the drive rod moved by movement of a first engagement feature.

The bag deployment device having an outer tube assembly which has an outer tube that encircles a portion of the drive rod and a stationary handle so a user can impart translation of the first engagement feature relative to the stationary handle. The outer tube assembly also having a pair of bag interface fingers located at the distal end of the outer tube adapted to engage the pair of spring openings in the collection bag as the spring arms are partially withdrawn into the outer tube.

This combination of features allowing the collection bag with the pair of spring openings containing the first spring arm and the second spring arm to be substantially closed by partially withdrawing the drive rod out the proximal end of the outer tube so that the pair of spring arms assumes a compressed position to substantially close the open end of the collection bag.

Some aspects of the teachings of the present disclosure may be expressed as a method of collecting an item during a surgical procedure from a surgical cavity. The method including the steps of:

obtaining a bag deployment device with an open end of a collection bag engaged with a pair of arms of at a distal end of the bag deployment device, the collection bag having a cinch loop pull string connected to a cinch loop around an open end of the collection bag with a proximal end of the cinch loop pull string accessible at a proximal end of the bag deployment device;

inserting a closed pair of arms at the distal end of the bag deployment device and the collection bag into a surgical cavity through an access cannula;

opening the closed pair of arms at the distal end of the bag deployment device to open an open end of the collection bag within the surgical cavity;

inserting an item into the open end of the collection bag;

closing the pair of arms at the distal end of the bag deployment device to substantially close the open end of the collection bag within the surgical cavity;

withdrawing the closed pair of arms at the distal end of the bag deployment device from the surgical cavity while leaving the collection bag within the surgical cavity;

the withdrawing of the closed pair of arms pulling a proximal portion of the cinch loop pull string connected to the cinch loop around the open end of the collection bag to substantially close the open end of the collection bag as the collection bag is being stripped from the distal end of the bag deployment device by the distal end of the access cannula; and removing the collection bag from the surgical cavity to retrieve the item in the collection bag.

Some aspects of the teachings of the present disclosure may be expressed as a method of delivering a collection bag to a surgical cavity. The method including the steps:

obtaining a bag deployment device with an open end of a collection bag engaged with a pair of arms of at a distal end of the bag deployment device;

inserting a closed pair of arms at the distal end of the bag deployment device and the collection bag into a surgical cavity through an access cannula;

transiting the access cannula without sheathing the collection bag in a tube to isolate the collection bag from an interior of the access cannula; and opening the closed pair of arms at the distal end of the bag deployment device to open an open end of the collection bag within the surgical cavity.

Other systems, methods, features and advantages of the disclosed teachings will be immediately apparent or will become apparent to one with skill in the art upon examination of the following figures and detailed description. It is intended that all such additional systems, methods, features and advantages be included within the scope of and be protected by the accompanying claims.

BRIEF DESCRIPTION OF THE FIGURES

The disclosure can be better understood with reference to the following figures. The components in the figures are not necessarily to scale, emphasis instead being placed upon illustrating the principles of the disclosure. Moreover, in the figures, like reference numerals designate corresponding parts throughout the different views.

FIG. 17 shows a flowchart of the process 1000 of using the bag deployment device to capture a specimen within a collection bag.

DETAILED DESCRIPTION

The presently disclosed subject matter is described with specificity to meet statutory requirements. However, the description itself is not intended to limit the scope of this patent. Rather, the inventors have contemplated that the claimed subject matter might also be embodied in other ways, to include different steps or elements similar to the ones described in this document, in conjunction with other present or future technologies. Moreover, although the term "step" may be used herein to connote different aspects of methods employed, the term should not be interpreted as implying any particular order among or between various steps herein disclosed unless and except when the order of individual steps is explicitly described.

Figure 1:
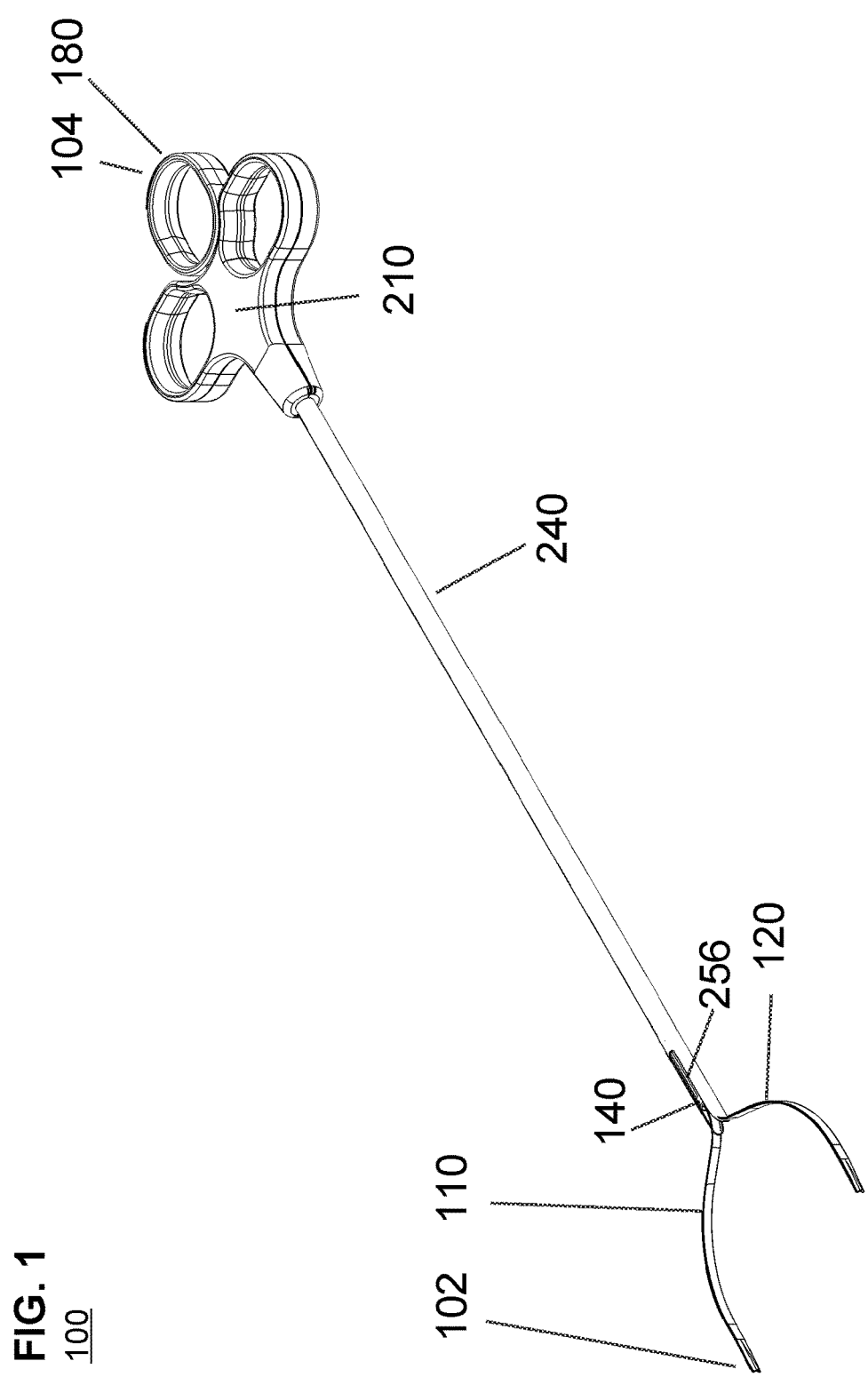
FIG. 1 shows an isometric view of a bag deployment device 100 with a distal end 102 for insertion into the patient and a proximal end 104 opposite from the distal end 102.

FIG. 1 shows an isometric view of a bag deployment device 100 with a distal end 102 for insertion into the patient and a proximal end 104 opposite from the distal end 102. Visible in FIG. 1 are the first spring arm 110, second spring arm 120, thumb engagement feature 180, stationary handle 210, and outer tube 240. While the first spring arm 110 and second spring arm 120 can be characterized as forming a wishbone, other shapes for a pair of spring arms are possible.

Figure 2:
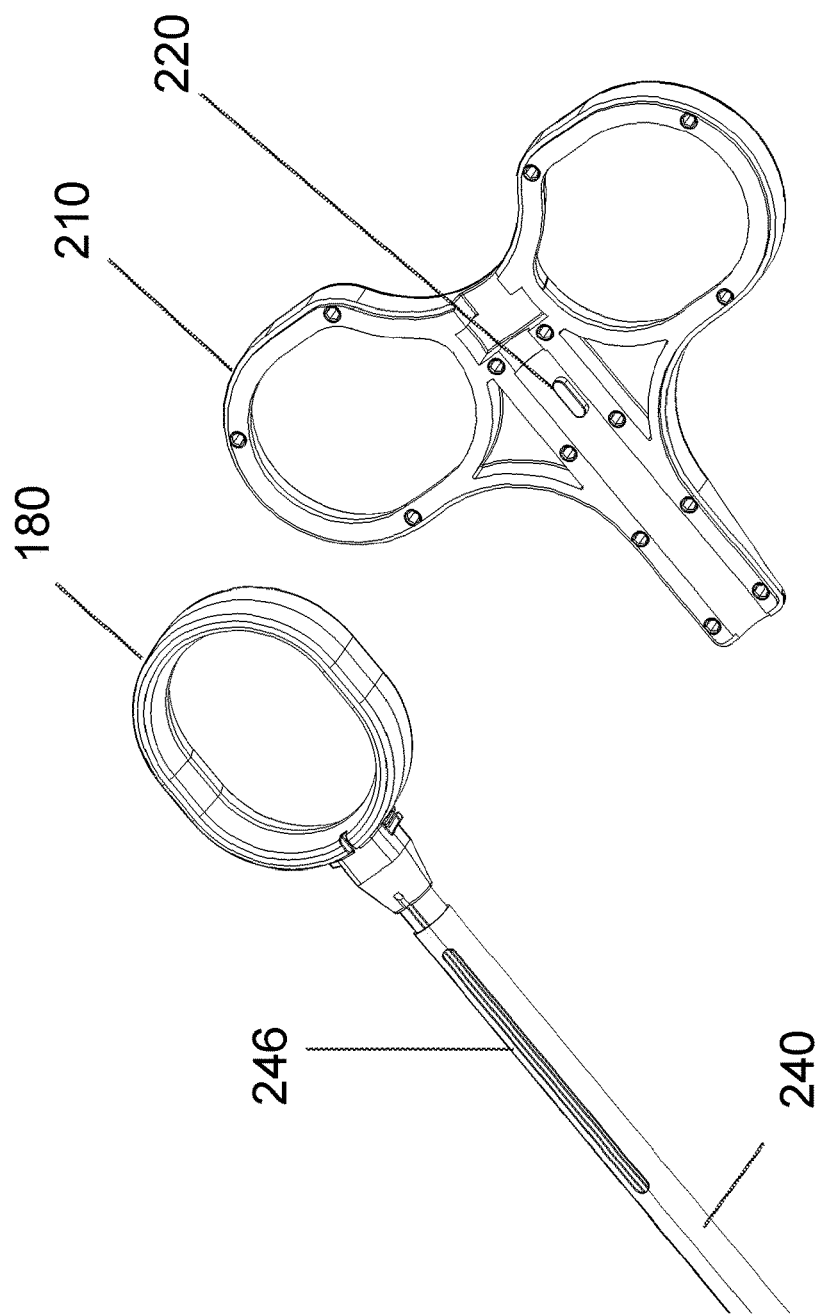
FIG. 2 shows the top part of the stationary handle 210 turned over to show handle protrusion 220.

FIG. 2 shows the top part of the stationary handle 210 turned over to show handle protrusion 220. Handle protrusion 220 engages with slot 246 in outer tube 240 and a slot 146 (not visible here) in drive rod 140 (not visible here) to limit the relative motion of the stationary handle 210 and the outer tube 240 and attached thumb engagement feature 180. The purpose and interactions of these components will be better understood after introduction of additional components in subsequent drawings.

Figure 3:
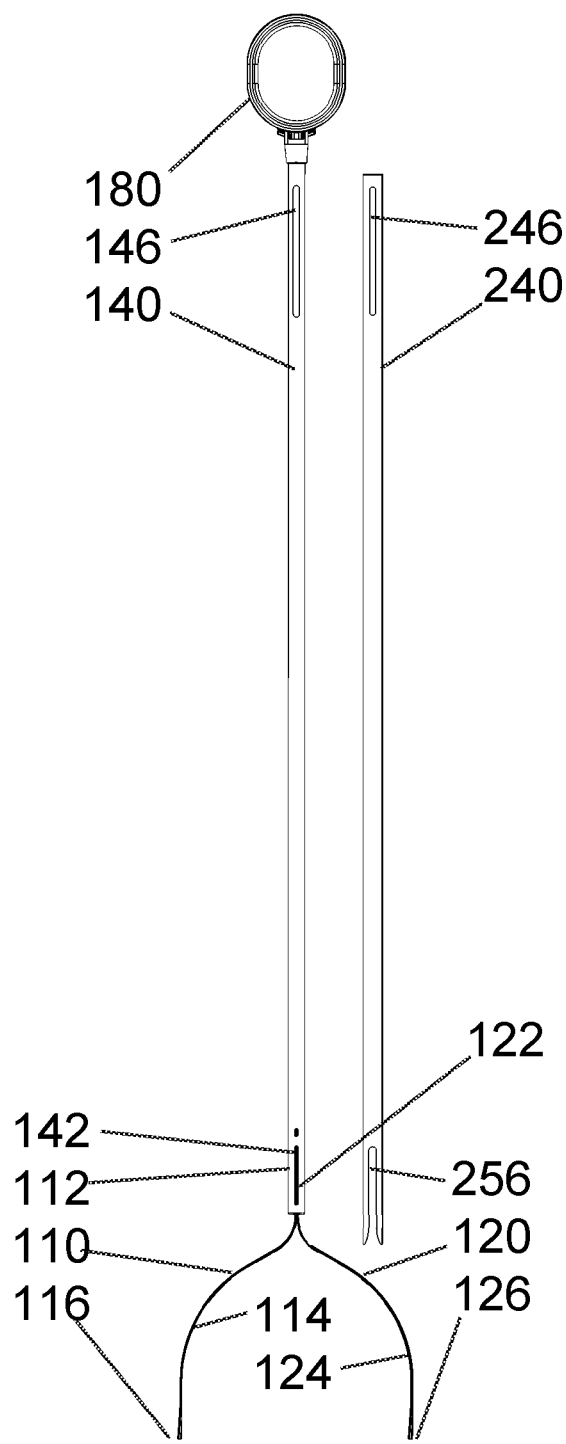
FIG. 3 is a top view of the bag deployment device 100 with the stationary handle 210 rendered invisible and the outer tube 240 moved to the right.

FIG. 3 is a top view of the bag deployment device 100 with the stationary handle 210 rendered invisible and the outer tube 240 moved to the right. Thumb engagement feature 180 is attached to drive rod 140 with slot 146. Outer tube 240 has slot 246 so that the handle protrusion 220 (FIG. 2) can interact with slot 146 to limit the relative motion of drive rod 140 relative to outer tube 240.

Visible in FIG. 3 are first spring arm 110 which has a substantially straight portion 112, a curved intermediate portion 114, and a distal tip 116. Second spring arm 120 has a corresponding shape. The two spring arms may be attached to the drive rod 140 by placing the substantially straight portions 112 and 122 in a slot 142 in the distal end of the drive rod 140. The spring arms 110 and 120 may be connected to the drive rod by any method known to those of skill in the art including pins, clips, welding, adhesives, chemical bonding, or other attachment techniques.

Not visible in FIG. 3 is a string channel 158 located in the outer perimeter of the drive rod 140. The string channel 158 allows a cinch loop pull string (discussed below) to fit within the string channel 158 so that the cinch loop pull string runs between a collection bag placed on the pair of spring arms 110 and 120 and the proximal end 104 of the bag deployment device 100 for use in cinching the collection bag in a substantially closed position. The string channel may extend through a portion of the thumb engagement feature 180 so a continuous channel runs from an outside surface of the thumb engagement feature 180 to the distal end 148 of the drive rod 140.

Figure 4:
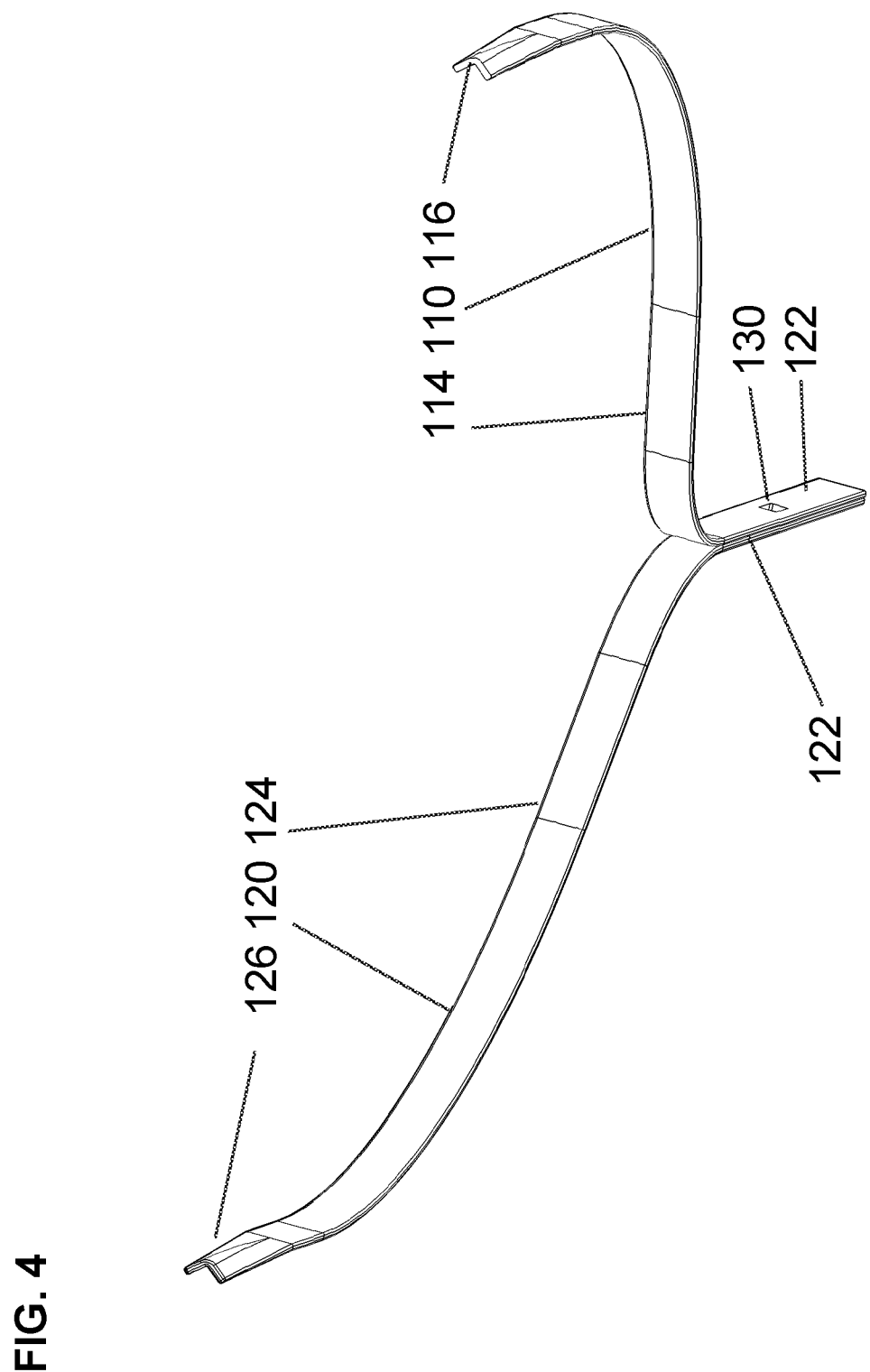
FIG. 4 shows a top rear perspective view of just the pair of spring arms 110 and 120.

FIG. 4 shows a top rear perspective view of just the pair of spring arms 110 and 120. Note that spring arm 110 has a distal tip 116 which is concave relative to the straight portion 112. In contrast, spring arm has a distal tip 126 which is convex relative to the straight portion 122. This combination allows distal tip 116 to nest over distal tip 126 when the tips are placed next to one another. When the bag deployment device 100 is in the closed position, distal tip 126 is interlocked via firm contact with distal tip 116 to provide superior resistance to shearing and scissoring. An advantage of this set of shapes for the distal tips is that the distal tips 116 and 126 interact to reduce the chances that one distal tip would cross over or under the other distal tip.

Those of skill in the art will recognize that the distal tips 116 and 126 could be flat or have other shapes but the nesting feature of the distal tips is thought to be a good choice. It is desirable that the distal tip 116 and 126 of the spring arms 110 and 120 engage with one another so that the spring arms 110 and 120 assume the flattened closed position rather than cross over to form a scissor position. One of skill in the art will recognize that an incident wherein the spring arms 110 and 120 scissor (cross over) would interfere with insertion of the bag deployment device 100 and engaged collection bag 300 into an access cannula 400 as discussed below.

Each spring arm 110 and 120 may have an engagement window 130 to engage with an engagement tab located in the slot 142 of the drive rod 140. The engagement window 130 on spring arm 110 need not be at the same insertion depth as the engagement window 130 on spring arm 120. As noted above, the connection of the spring arm to the drive rod can be achieved by a number of conventional ways known to those of skill in the art.

Figure 5:
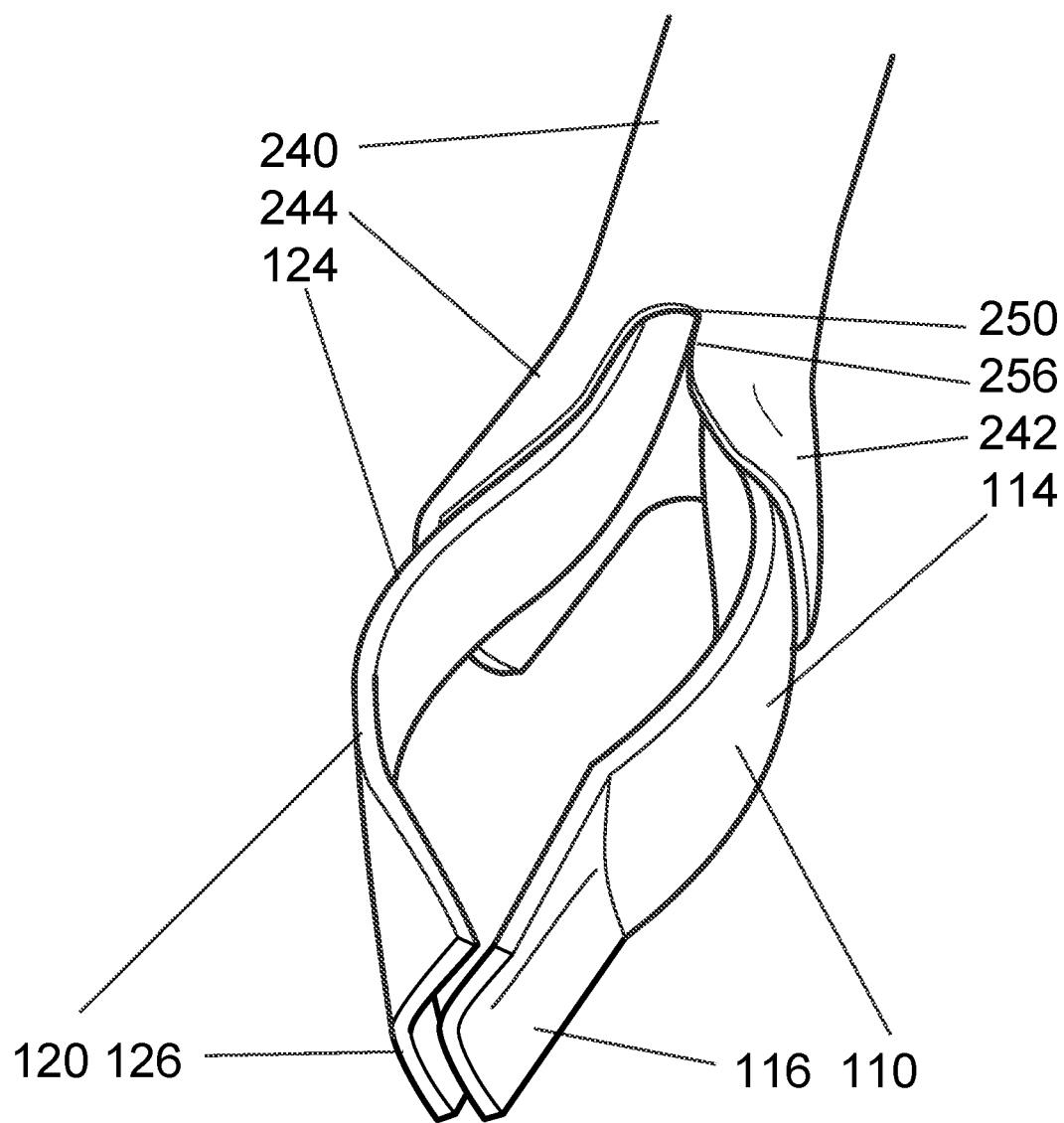
FIG. 5 shows a front top perspective view of distal tips 116 and 126 in a closed position as the drive rod 140 (not visible here) has been retracted within the outer tube 240 to press the distal tips 116 of spring arm 110 into distal tip 126 of spring arm 120.

FIG. 5 shows a front top perspective view of distal tips 116 and 126 in a closed position as the drive rod 140 (not visible here) has been retracted within the outer tube 240 to press the distal tips 116 of spring arm 110 into distal tip 126 of spring arm 120. If the spring arms 110 and 120 were engaged with a collection bag 300 (discussed below), the open end of the collection bag 300 would be substantially closed by the collapsed spring arms 110 and 120.

Movement of Spring Arms to Closed Position.

FIG. 1 shows the distal end 102 of bag deployment device 100 with the outer tube 240 partially encircling the drive rod 140. The encircling is partial as drive rod 140 is not fully encircled at finger slot 256 (seen in more detail in FIG. 5). FIG. 5 differs from FIG. 1 in that the thumb engagement feature 180 (FIG. 1) has been moved proximally relative to the stationary handle 210 to pull the drive rod 140 distally relative to the outer tube 240 which is connected to the stationary handle 210. This proximal movement of the drive rod 140 pulls the attached spring arms 110 and 120 in the proximal direction and causes the first bag interface finger 242 and the second bag interface finger 244 to push against curved intermediate portions 114 and 124 of the pair of spring arms 110 and 120 to bring the distal tip 116 of first spring arm 110 into contact with distal tip 126 of second spring arm 120. Thus, the spring arms 110 and 120 move from an open position resembling a spring as shown in FIG. 1, to a closed position with the distal tips 116 and 126 in contact or proximity as shown in FIG. 5.

Those of skill in the art will appreciate that the movement of the distal tips 116 and 126 of the spring arms 110 and 120 could be achieved with a simple cylindrical distal end of outer tube 240. As best seen in FIG. 5, the outer tube 240 has a pair of bag interface fingers, more specifically the first bag interface finger 242 and the second bag interface finger 244, separated by a finger slot 256 rather than a simple cylindrical end. Note that the movement of a simple cylindrical end towards the collection bag 300 would tend to strip the collection bag 300 from the spring arms 110 and 120. The innovative use of the bag interface fingers 242 and 244 is discussed in more detail below.

Figure 6:
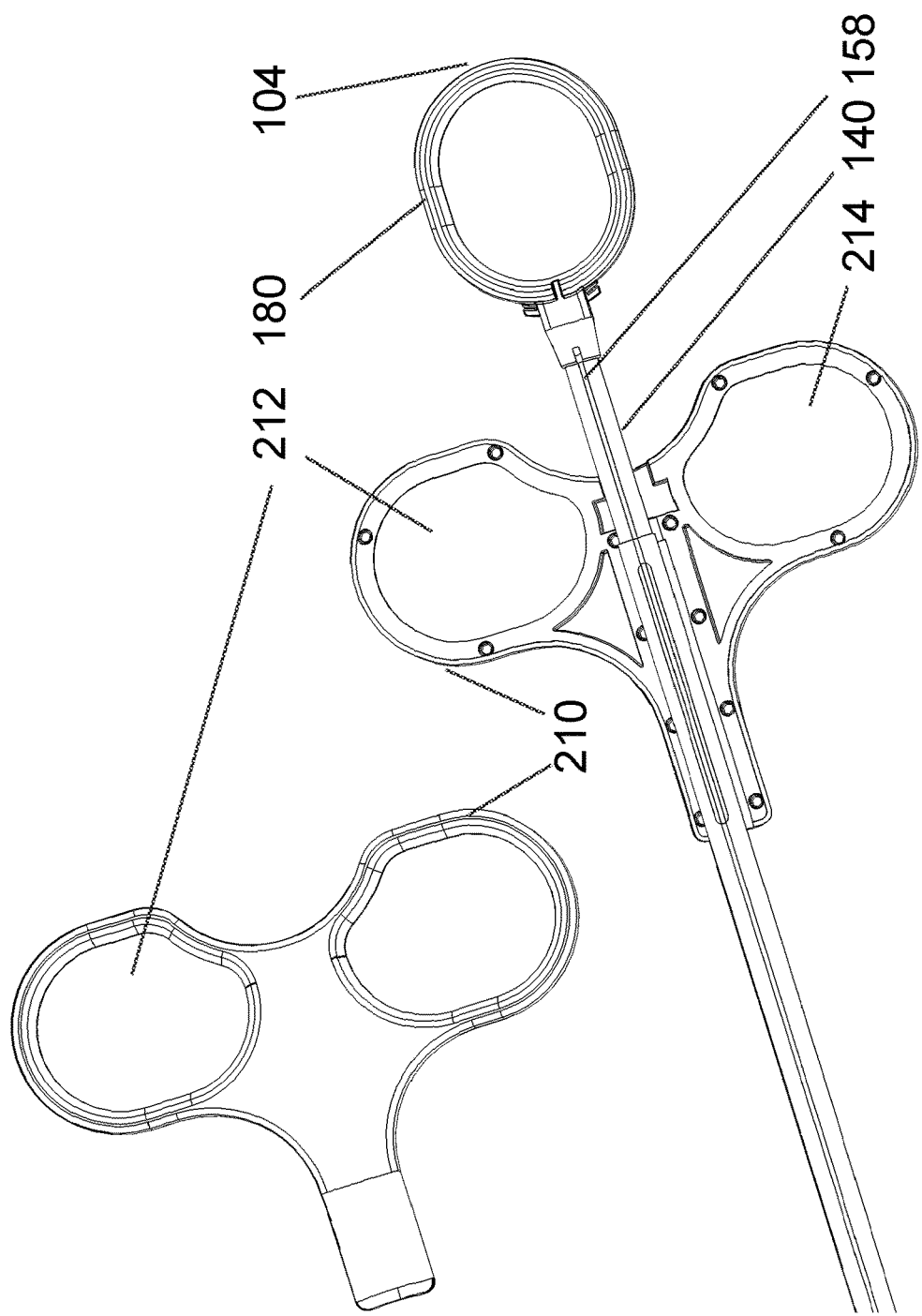
FIG. 6 shows the proximal end 104 of the bag deployment device 100 with the thumb engagement feature 180 moved in a proximal direction away from the stationary handle 210 having a first finger engagement opening 212 and a second finger engagement opening 214.

FIG. 6 shows the proximal end 104 of the bag deployment device 100 with the thumb engagement feature 180 moved in a proximal direction away from the stationary handle 210 having a first finger engagement opening 212 and a second finger engagement opening 214. To assist with this discussion, the top portion of the stationary handle 210 has been removed and positioned close to the other components. The movement of the thumb engagement feature 180 moves the connected drive rod 140 in the proximal direction to withdraw a portion of the drive rod 140 from the proximal end of the stationary handle 210. As previously noted, the amount of relative motion is limited by handle protrusion 220 (FIG. 2) and slot 146 (best seen in FIG. 3)

Visible in FIG. 6 is string channel 158 that runs along the drive rod 140 and within the outer tube 240 to allow a cinch loop pull string 350 (discussed below) to be within the confines of the outer tube 240 so that insertion of the distal portions of the bag deployment device 100 through an access cannula can be done while protecting the cinch loop pull string 350 placed in the string channel 158. The proximal end of the cinch loop pull string 350 may be engaged to the thumb engagement feature 180 or otherwise engaged with something at the proximal end 104 of the bag deployment device 100.

Process of Use.

Now that the various components have been introduced, it is possible to step through a demonstration of bag deployment and use.

Figure 7:
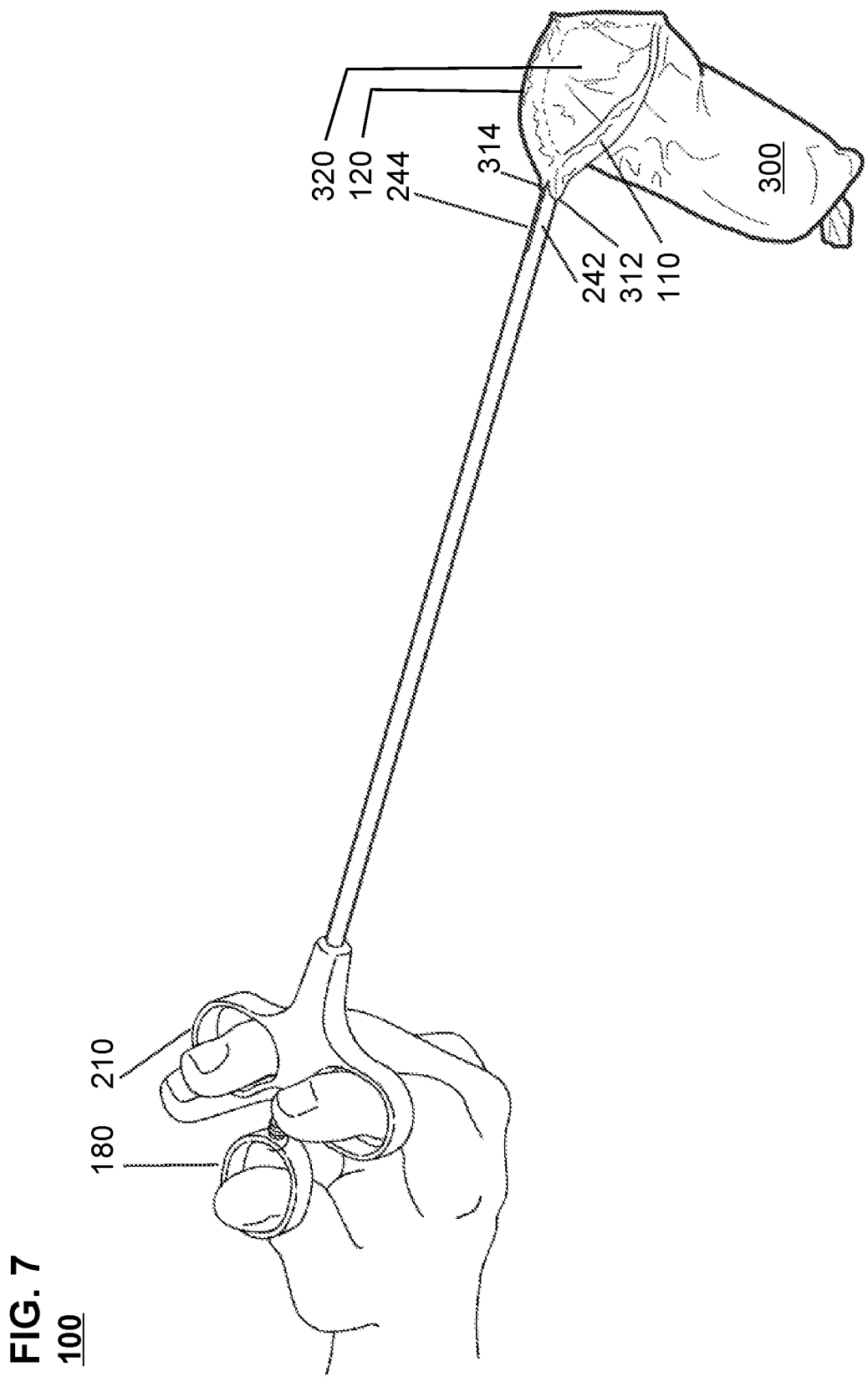
FIG. 7 shows a bag deployment device 100 with spring arms 110 and 120 is holding open the open end 320 of a collection bag 300.

In FIG. 7, a bag deployment device 100 with spring arms 110 and 120 is holding open the open end 320 of a collection bag 300. Notice that the thumb engagement feature 180 is positioned distally against the stationary handle 210.

Figure 8:
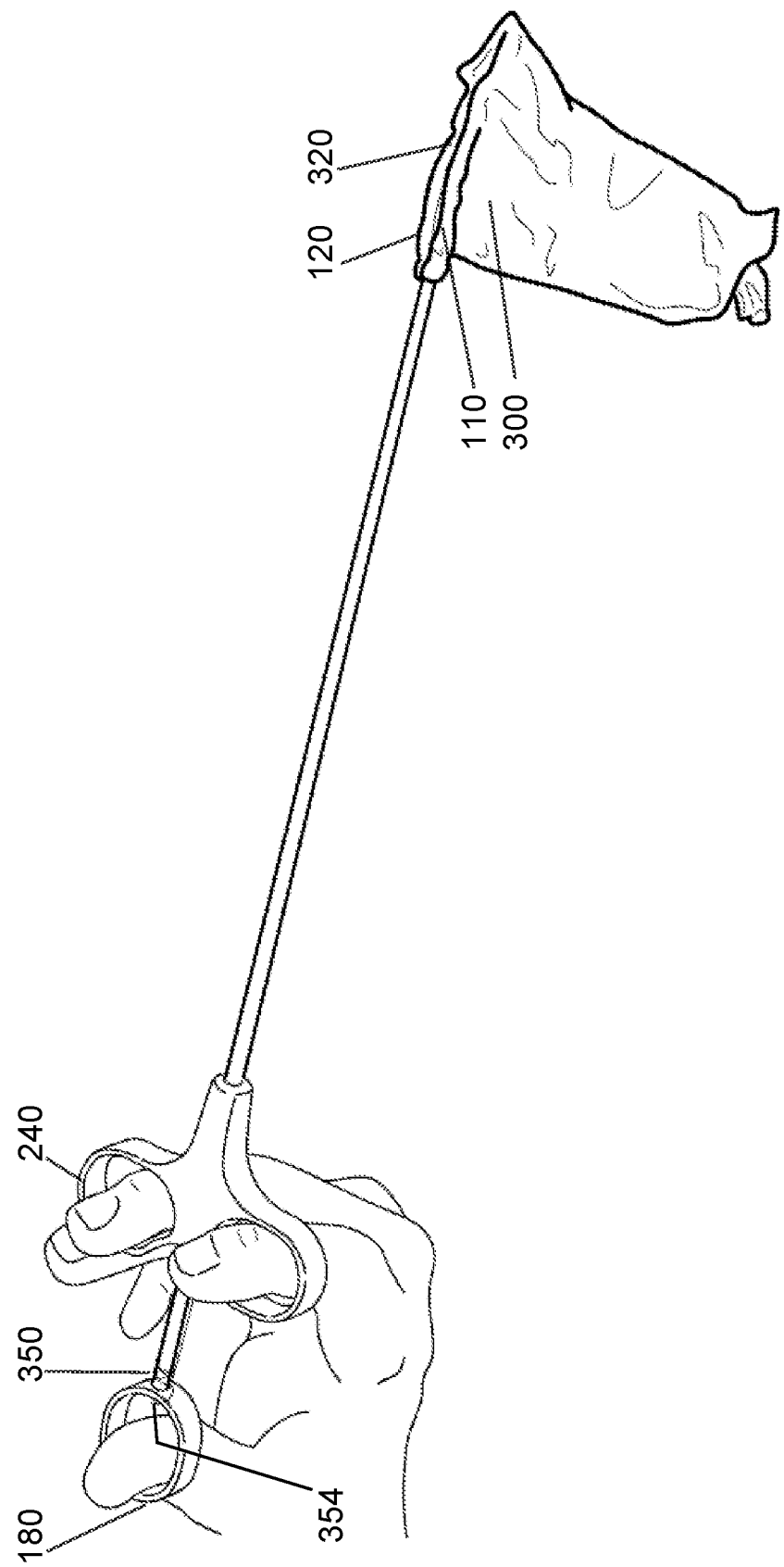
FIG. 8 shows the thumb engagement feature 180 after moving proximally relative to the stationary handle 210 to close the pair of spring arms 110 and 120 and substantially close the open end 320 of the collection bag 300.

FIG. 8 shows the thumb engagement feature 180 after moving proximally relative to the stationary handle 210 to close the pair of spring arms 110 and 120 and substantially close the open end 320 of the collection bag 300. Bag interface fingers 242 and 244 have pressed the spring arms 110 and 120 together as the bag interface fingers 242 and 244 have entered within first spring opening 312 and second spring opening of the collection bag 300. Although hidden here by unified bag pathway 316 of the collection bag 300, the distal tip 116 and distal tip 126 are engaged with one another as shown in detail in FIG. 5. The cinch loop pull string 350 is running within outer tube 240 in string channel 158 (See FIG. 6) to proximal of the stationary handle 210 and is secured to the proximal end of the cinch loop pull string 350 to the drive rod 140 adjacent to the thumb engagement feature 180.

Figure 9:
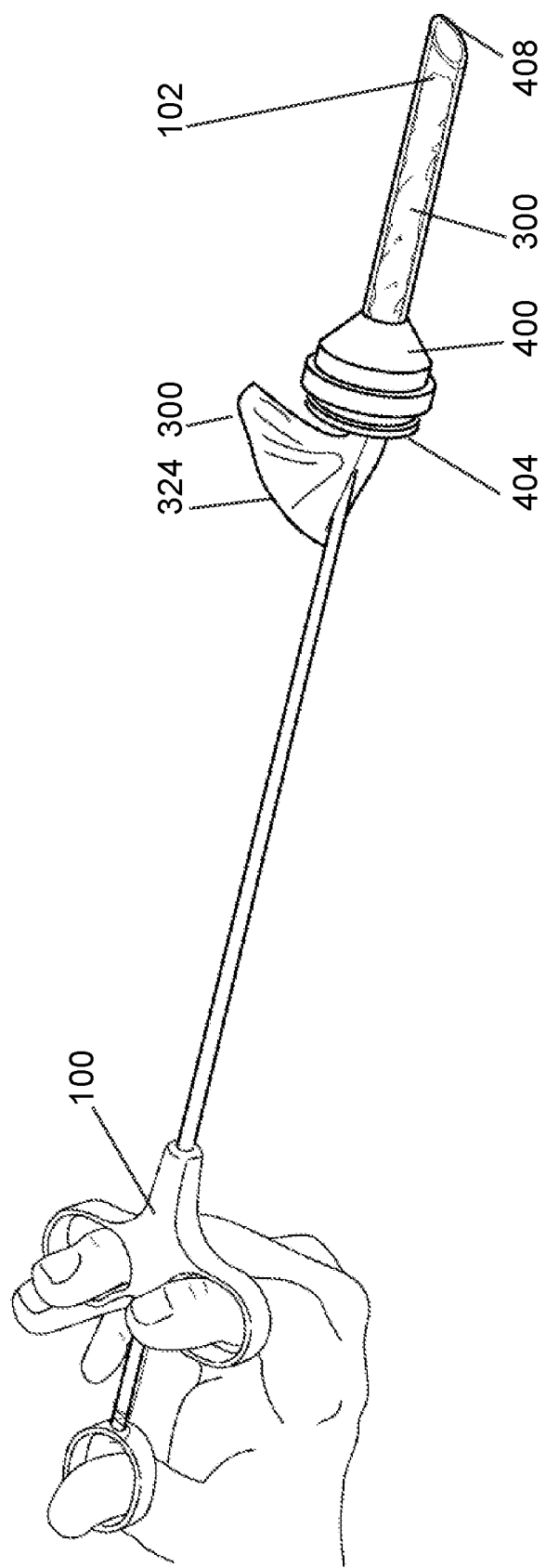
FIG. 9 shows the distal end 102 of the bag deployment device 100 with spring arms 110 and 120 in the closed position and an engaged and substantially closed collection bag 300 is now inserted through a proximal end 404 of an access cannula 400 into a body cavity for use in collecting a specimen from a surgical procedure.

In FIG. 9, the distal end 102 of the bag deployment device 100 with spring arms 110 and 120 in the closed position and an engaged and substantially closed collection bag 300 is now inserted through a proximal end 404 of an access cannula 400 into a body cavity for use in collecting a specimen from a surgical procedure. The access cannula 400 is sometimes called an access port. In actual operation, the access cannula 400 would be already positioned along the surgical access path and holding open an access channel for access by surgical tools. For this disclosure, the access cannula 400 is simply shown independent of the patient and the surgical site. While the present disclosure may be scaled for use in a variety of surgical procedures in human and animal patients, for sense of scale, the sequence of drawings in FIG. 7 through FIG. 16 are for a bag deployment device 100 and collection bag 300 for use in an access cannula 400 with an interior diameter on the order of magnitude of 10 mm or slightly larger.

The distal tips 116 and 126 (FIG. 5) of the spring arms 110 and 120 (FIG. 5) enter the proximal end 404 of the access cannula 400. As the distal tips 116 and 126 (FIG. 5) of the spring arms 110 and 120 continue to traverse the interior of the access cannula 400, the rest of the collection bag 300 including closed end 324 follows the open end 320 of the collection bag 300 through the proximal end 404 of the access cannula 400.

Notice that unlike other prior art solutions, the collection bag 300 is not withdrawn into a delivery tube and then shielded from contact with the access cannula 400 as the distal end of the extra delivery tube is passed through the interior of the access cannula 400.

Figure 10:
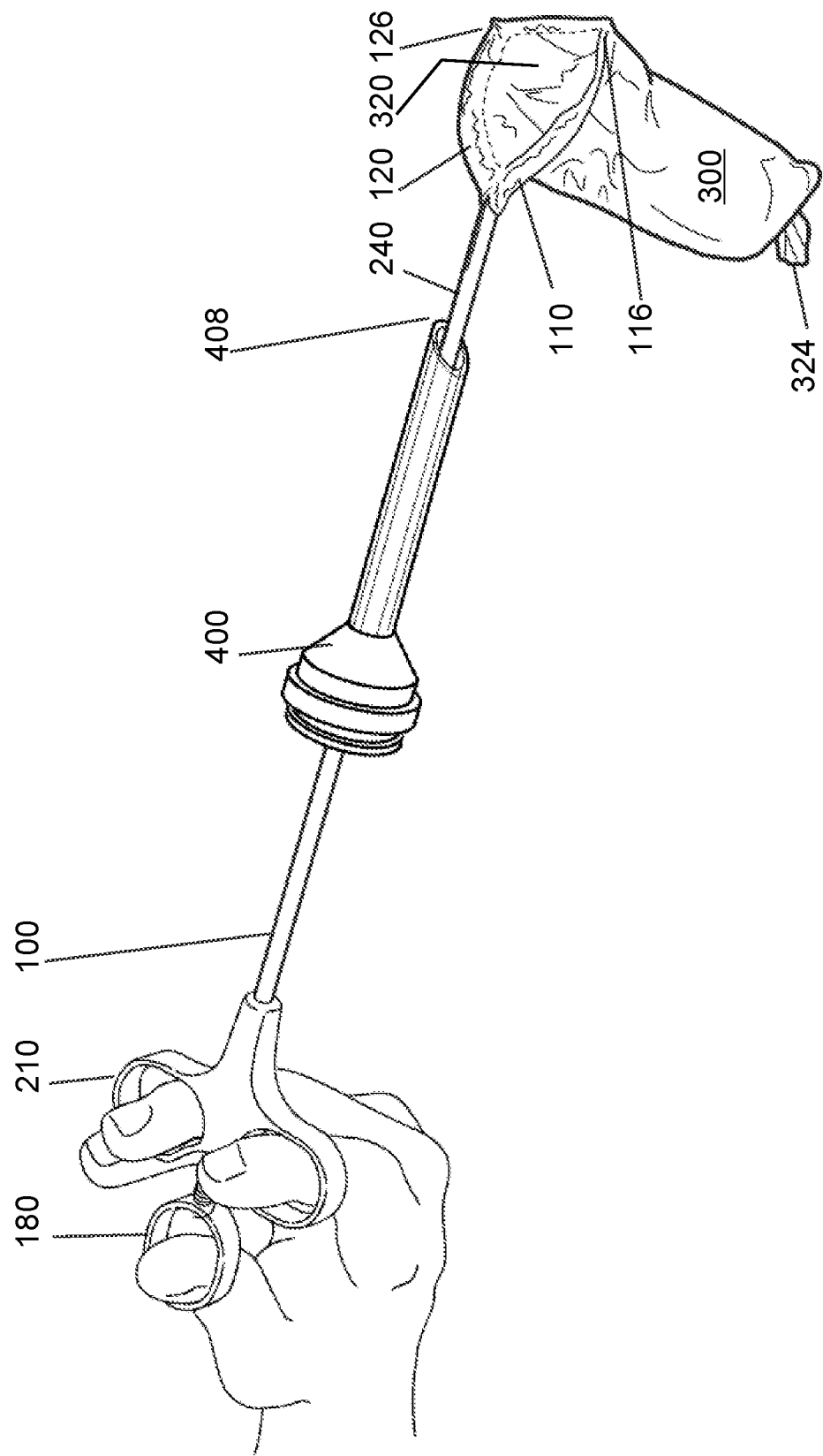
FIG. 10 shows the spring arms 110 and 120 of the bag deployment device 100 have been inserted past the distal end 408 of the access cannula 400.

FIG. 10 shows the spring arms 110 and 120 of the bag deployment device 100 have been inserted past the distal end 408 of the access cannula 400. Once the trailing closed end 324 of the collection bag 300 leaves the distal end 408 of the access cannula 400, the collection bag 300 is now fully inserted in the body cavity beyond the access cannula 400. Subsequently, the thumb engagement feature 180 has been moved distally relative to the stationary handle 210. As described above, this imparts relative motion of the drive rod 140 relative to the outer tube 240 so that the spring arms 110 and 120 extend and open the open end 320 of the collection bag 300.

This demonstration of the bag deployment device 100 does not include the insertion of a specimen into the collection bag as one of skill in the art can envision placement of an object through the open pair of spring arms 110 and 120 into the collection bag 300 and there is no intent to limit the type of specimen or other payload inserted into the collection bag 300. While in most instances the collection bag 300 will be used for collection of a specimen from a patient undergoing surgery, the collection bag 300 could be used to collect some other item such as a foreign body present within the patient.

Figure 11:
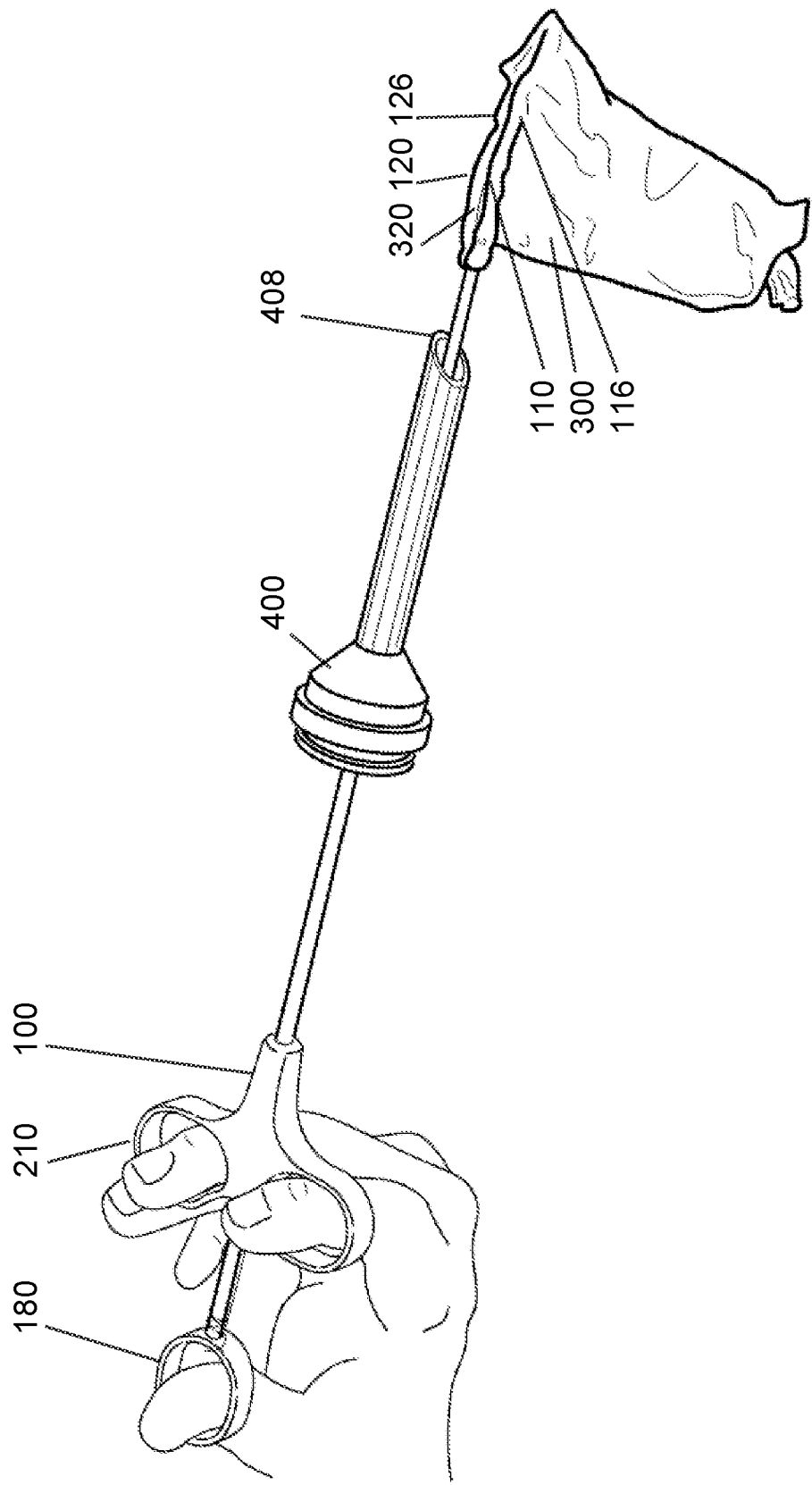
FIG. 11 shows the closure of the collection bag 300 after insertion of the payload into the collection bag 300.

FIG. 11 shows the closure of the collection bag 300 after insertion of the payload into the collection bag 300. The thumb engagement feature 180 has been moved proximally relative to the stationary handle 210. As described above, this imparts relative motion of the drive rod 140 relative to the outer tube 240 so that the spring arms 110 and 120 close the open end 320 of the collection bag 300 and interlock the distal tips 116 and 126. Note that the closure of the open end 320 of the collection bag 300 does not involve any interaction with the distal end 408 of the access cannula 400.

As discussed in connection with FIG. 7, the first bag interface finger 242 and second bag interface finger 244 located on the outer tube 240 are within the first spring arm opening 312 and second spring arm opening 314 of the collection bag.

Figure 12:
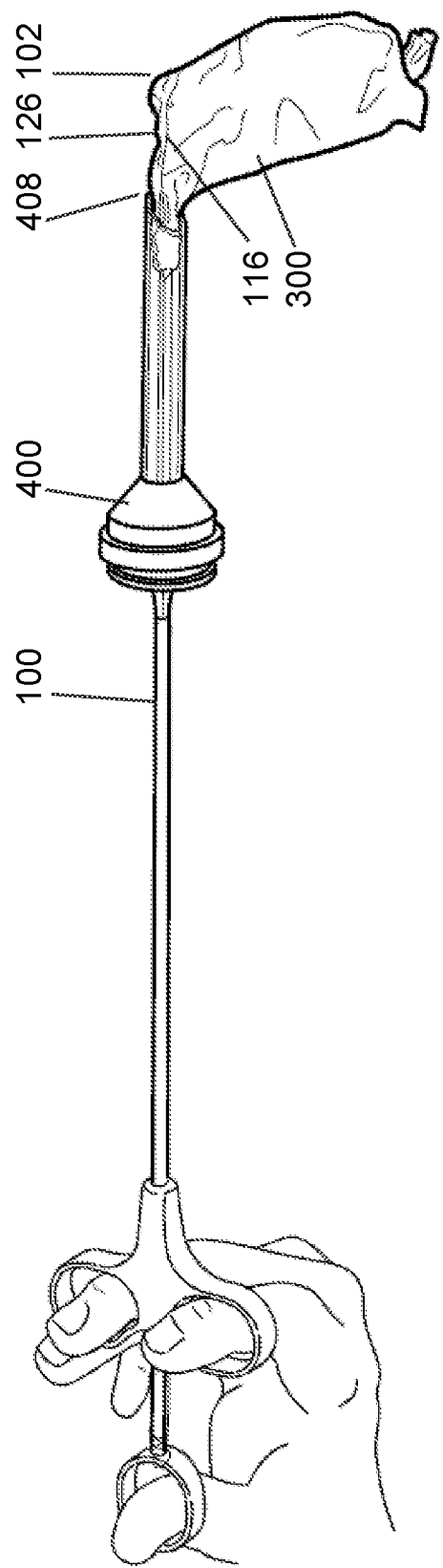
FIG. 12 shows the retraction of the distal end 102 closed bag deployment device 100 through the distal end 408 of the access cannula 400.

FIG. 12 shows the retraction of the distal end 102 closed bag deployment device 100 through the distal end 408 of the access cannula 400. As the distal end 102 of the bag deployment device 100 is withdrawn into the distal end 408 of the access cannula 400, the substantially closed collection bag 300 is stripped off the distal end 102 of the bag deployment device 100 by the distal end 408 of the access cannula 400 as the first bag interface finger 242 and second bag interface finger 244 are pulled proximally and slip out of the first spring arm opening 312 and the second spring arm opening 314 of the the open end 320 of the collection bag 300 (See FIG. 15 and FIG. 16).

Figure 13:
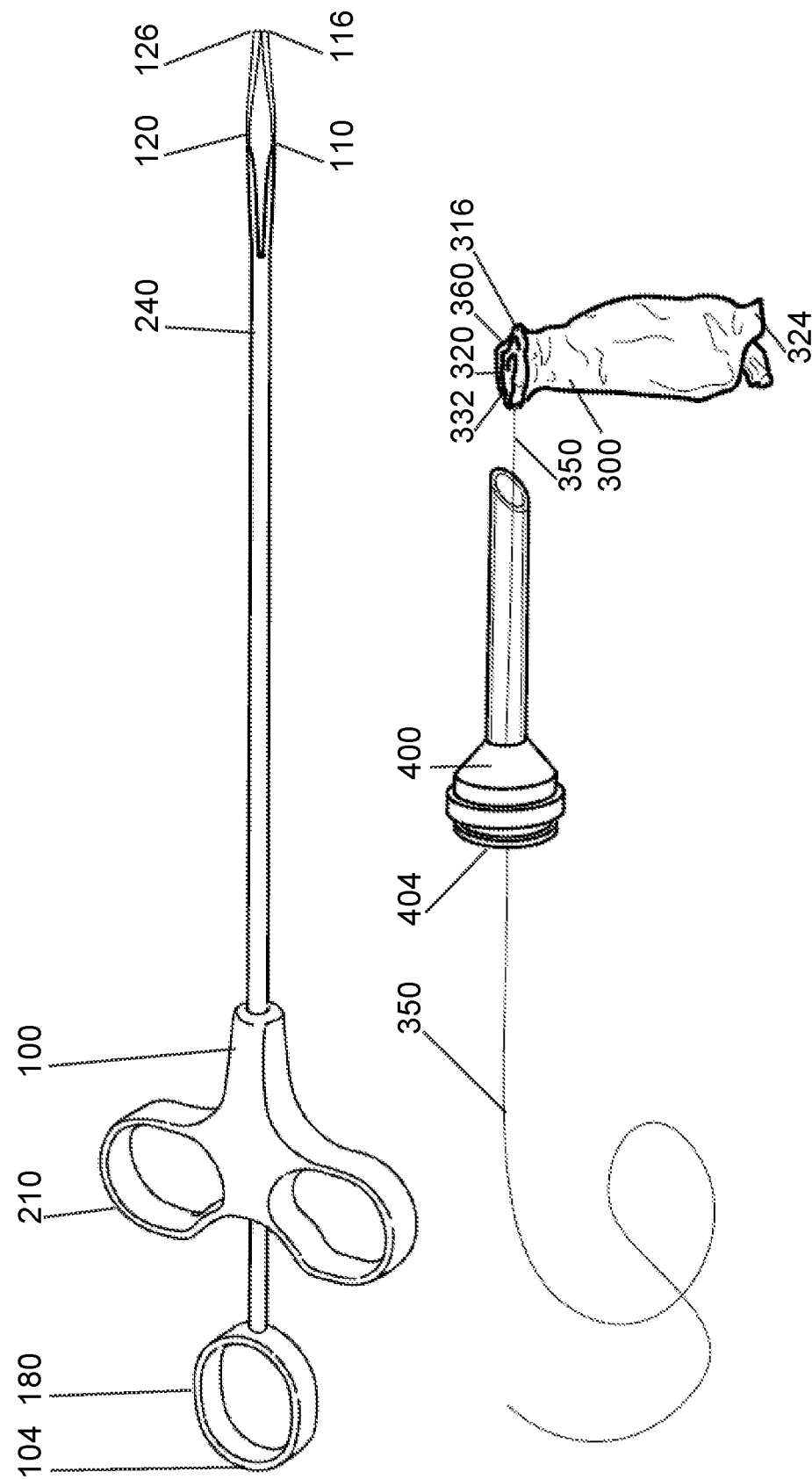
FIG. 13 shows the cinch loop pull string 350 after the disconnecting from near the proximal end 104 of the bag deployment device 100.

Looking at FIG. 12 and FIG. 13, one can appreciate that pulling the proximal end 104 of the bag deployment device 100 away from the collection bag 300 which is retained at the distal end 408 of the access cannula 400 simultaneously pulls the cinch loop pull string 350. This causes the cinch loop 360 in the cinch loop pull string 350 to decrease in area within the unified bag pathway 316 around the bag open perimeter 332 to cinch closed the open end 320 of the collection bag 300 to secure the specimen within the collection bag 300. Note that the cinch operation need only substantially close the open end 320 and a small residual opening is not a problem.

The process pulls the collection bag 300 to the open distal end 408 of the access cannula 400 but the collection bag 300 cannot traverse the access cannula 400 in the proximal direction. The collection bag 300 will not be pulled though the distal end 408 of the access cannula 400 as the first bag interface finger 242 and the second bag interface finger 244 will slip out of the first spring opening 312 and second spring opening 314 leaving the collection bag 300 in the body cavity as the cinch loop pull string 350 begins to cinch the cinch loop 360 to close the unified bag pathway 316 around the bag open perimeter 332 to substantially close the open end 320 of the collection bag 300.

Eventually, the distal tips 116 and 126 of the first and second spring arms 110 and 120 are withdrawn into the distal end 408 of the access cannula 400 and the collection bag 300 is only connected to the bag deployment device 100 by the cinch loop pull string 350 running in the string channel 158 (FIG. 6) along the exterior of the drive rod 140 within the outer tube 240. A proximal end 354 of the cinch loop pull string 350 is still connected to or near the thumb engagement feature 180.

The proximal end 354 of the cinch loop pull string 350 can now be released from the proximal end of the bag deployment device 100 to allow the removal of the distal end 102 of the bag deployment device 100 from the proximal end 404 of the access cannula 400.

FIG. 13 shows the state of affairs after the bag deployment device 100 has been pulled out of the proximal end 404 of the access cannula 400. The distal tips 116 and 126 of the two spring arms 110 and 120 have been pulled out the proximal end 404 of the access cannula 400 and the entire bag deployment device 100 is clear of the access cannula 400 with the cinch loop pull string 350 initially still connected to the collection bag 300 (as seen in FIG. 12). FIG. 13 shows the cinch loop pull string 350 after the disconnecting from near the proximal end 104 of the bag deployment device 100. The bag deployment device 100 may be set down as it is no longer needed.

The cinched collection bag 300 may be removed immediately or may drop into the body cavity until the end of the procedure.

Those of skill in the art will recognize that the cinched collection bag 300 may be withdrawn through the access cannula 400 or the access cannula 400 may be withdrawn from the patient and the cinched collection bag 300 may be withdrawn through the access channel to the body cavity which would be larger than the interior diameter of the access cannula 400. If necessary, the opening into the patient may be increased slightly with a scalpel or other appropriate tool to allow easy removal of the cinched collection bag 300 by pulling on the cinch loop pull string 350 or through use of an appropriate tool to grab the cinched collection bag 300 and pull it through the opening in the patient.

Figure 14:
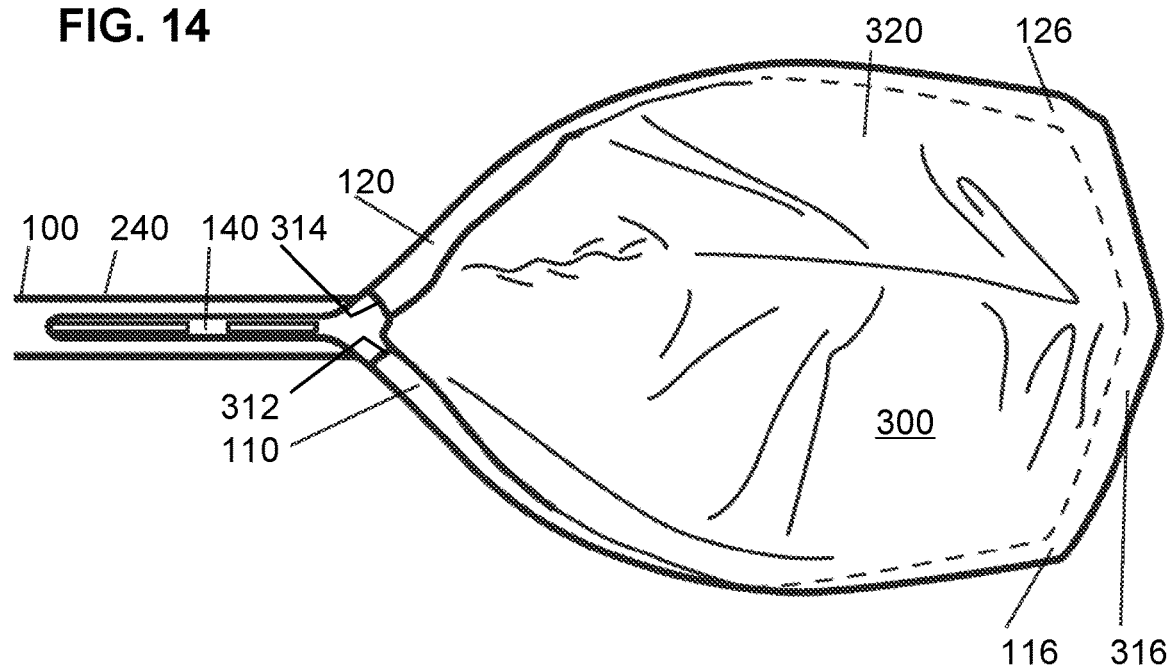
FIG. 14 shows a top view of the bag deployment device 100 with an engaged collection bag 300 in the open position.
Figure 15:
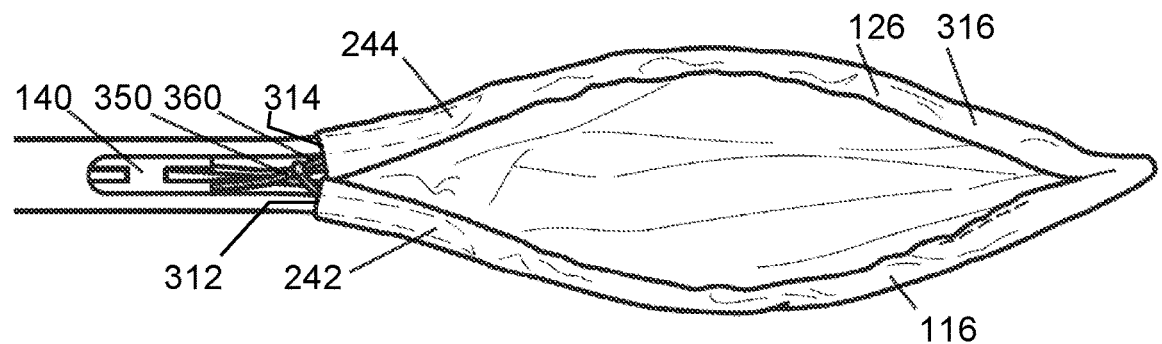
FIG. 15 shows the drive rod 140 being retracted towards the proximal end 104 of the bag deployment device 100 so that the distal tip.
Figure 16:
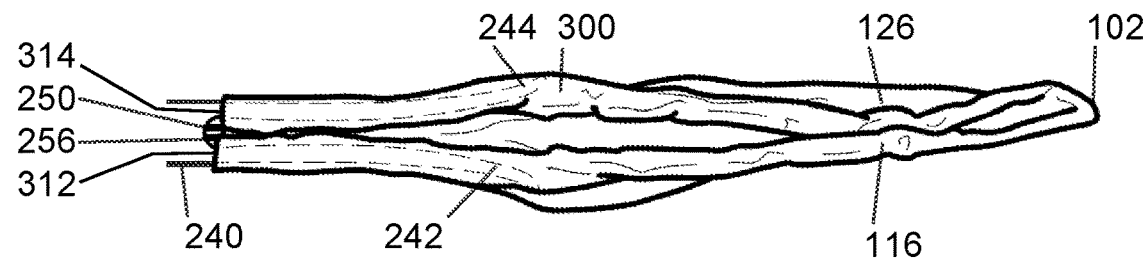
FIG. 16 shows the collection bag 300 after additional proximal movement of the drive rod 140 as the first bag interface finger 242 and the second bag interface finger 244 simultaneously push the first spring arm 110 and the second spring arm 120 into the closed position.

FIG. 14, FIG. 15, and FIG. 16 show a sequence of the spring arms 110 and 120 being withdrawn into the distal end of the outer tube 240 and the closing of the open end 320 of the collection bag 300.

FIG. 14 shows a top view of the bag deployment device 100 with an engaged collection bag 300 in the open position. Note that the first bag interface finger 242 and the second bag interface finger 244 may be totally outside of the unified bag pathway 316 when the collection bag 300 is in the open position.

FIG. 15 adds the detail of cinch loop pull string 350 connected to cinch loop 360. Relative to FIG. 14, FIG. 15 shows the drive rod 140 being retracted towards the proximal end 104 of the bag deployment device 100 so that the distal tip 116 is moving towards distal tip 126 as the open end 320 is closing.

As the spring arms 110 and 120 are retracted, the first bag interface finger 242 and the second bag interface finger 244 (shown in dashed lines in unified bag pathway 316) extend deeper beyond spring arm openings 312 and 314 until collection bag 300 is in the closed position shown in FIG. 16.

FIG. 16 shows the collection bag 300 after additional proximal movement of the drive rod 140 as the first bag interface finger 242 and the second bag interface finger 244 simultaneously push the first spring arm 110 and the second spring arm 120 into the closed position. The first spring arm opening 312 of collection bag 300 continues to move in a proximal direction as it remains engaged with first bag interface finger 242 (shown in dashed outline within unified bag pathway 316) and second spring arm opening 314 interacts with second interface finger 244 (shown in dashed outline within unified bag pathway 316).

The length of the first bag interface finger 242 and the second bag interface finger 244 is chosen to provide adequate support for the compression of the first spring arm 110 and the second spring arm 120 to the closed position.

At the end of FIG. 16, the drive rod 140 is fully retracted relative to the outer tube 240 and the bag deployment device 100 is ready to be retracted through the access cannula 400 (FIG. 12).

Note, the sequence of movement shown in FIG. 14, FIG. 15, and FIG. 16 would apply to closing the collection bag 300 before initial insertion through the access cannula 400 or to the closure of the collection bag 300 after collection of the item and before withdrawing the bag deployment device 100 through the access cannula 400.

Summary of Process.

FIG. 17 shows a flowchart of the process 1000 of using the bag deployment device to capture a specimen within a collection bag. It may be summarized as follows below.

1004—Obtain a bag deployment device with a collection bag loaded on the bag deployment device. The cinch loop pull string would normally be previously routed from the collection bag to the proximal end of the bag deployment device and be secured. While a tied endpoint is one viable option, the cinch loop pull string could be secured via a slit in the proximal end of the bag deployment device, a clamp, a piece of tape, or other mechanisms known to people of skill in the art. The bag deployment device and collection bag are likely to be sterilized prior to delivery for use.

1008—Remove protective packaging that maintains the sterility of the bag deployment device and the collection bag. The spring arms for the bag deployment device will be in the open position holding open the open end of the engaged collection bag.

1012—Close the spring arms so that the distal tips touch and the open end of the collection bag is substantially closed.

1016—With the spring arms still closed, insert the distal end of the bag deployment device and the engaged collection bag through and access cannula to deliver the collection bag to the body cavity for collection of a specimen. Note that the collection bag is not sheathed within a cannula before transit through the access cannula. Thus the collection bag is adjacent to the access cannula during the transit of the access cannula.

1020—Move the thumb engagement feature 180 distally to open the spring arms to open the open end of the collection bag.

1024—Place one or more items into the open end of the collection bag.

1028—Move the thumb engagement feature 180 proximally to close the spring arms to substantially close the open end of the collection bag.

1032—Retract the closed spring arms into the distal end of the access cannula. As the distal end of the bag deployment device recedes into the distal end of the access cannula, the collection bag is stripped from the distal end of the bag deployment device.

1036—Partially withdraw the distal end of the bag deployment device through the access cannula which pulls the proximal end of the cinch loop pull string away from the collection bag and cinches the open end of the collection bag so that the cinched bag remains substantially closed to retain the one or more specimens.

1040—Disconnect the cinch loop pull string 350 from the proximal end of the bag deployment device 100 and then the bag deployment device 100 may be fully withdrawn from the access cannula 400.

1044—The cinched collection bag is now located within the body cavity and ready for removal now or at a later stage of the surgical procedure.

1048—The cinched collection bag may be removed through the access cannula or the access cannula may be removed from the surgical site and then the cinched collection bag removed through the access channel that hosted the access cannula.

ALTERNATIVES AND VARIATIONS

Rings not Required.

The thumb engagement feature 180 shown and discussed above is a ring-shaped feature that may be manipulated to move in a proximal or distal direction by a user's thumb. Other shapes may be used such as a portion of a ring, a crossbar, or other shapes that can be manipulated by a user. It is not a requirement of the present disclosure that the thumb engagement feature be manipulated by the user's thumb although that is one option that was provided by this disclosure.

Likewise the example provided of a stationary handle 210 had a pair of rings for use as the first finger engagement opening 212 and a second finger engagement opening 214. Again, a ring shape is not required and could be replaced with a partial ring, or other shape that can be used to provide leverage to a user trying to move the thumb engagement feature 180 relative to the stationary handle 210. It is not a requirement that the stationary handle 210 be designed to engage with exactly two fingers of the user.

While some designers may implement an option for one-handed operation to move the thumb engagement feature 180 relative to the stationary handle 210, a design could be implemented that uses more than one hand to impart the relative motion and thus open and close the pair of spring arms 110 and 120.

Likewise, a designer may opt to use a device with a pistol grip which would allow for single-hand use by moving a trigger-type actuator to open and close the spring arms 110 and 120.

Alternatives to Thumbs.

This disclosure shows the movement of thumb engagement feature 180 relative to stationary handle 210. Those of skill in the art will recognize that relative motion can be imparted by motive forces other than the movement of a thumb relative to other fingers on the hand of a single user. This may become increasingly true when vocal commands to instruments become more commonplace. This may be true when the surgery is performed or assisted by robotic agents that have the capacity to impart relative motion without the use of something we might call a thumb. So the present disclosure should be viewed in terms of an imposition of a type of relative motion to open and close the spring handles without a focus on the way that relative motion is imparted to the bag deployment device.

Cinch Step May be Done after Release of Cinch Loop Pull String.

Although it may be convenient to have the cinch operation to cinch close the open end 320 of the collection bag 300 occur while the proximal end 354 of the cinch loop pull string 350 is still affixed to the proximal end 104 of the bag deployment device 100, this is not a requirement of the present disclosure. One could detach the proximal end 354 of the cinch loop pull string 350 from the proximal end 104 of the bag deployment device 100 before cinching the open end 320 of the collection bag 300.

Alternative Spring Tips.

In order to reduce the occurrence of crossover (scissoring) where the spring arms form an X rather than have the distal tips maintain contact, alternative distal tip designs may be used. The example set forth above had distal tip 116 a mirror image to distal tip 126. While mating tips is a viable solution, it is not a requirement of the present disclosure. The width of the distal tips 116 and 126 could be flared to reduce the likelihood of tip crossover. Those of skill in the art will be able to adapt the teachings of this disclosure to employ other tip interlock schemes. For example, one tip could have a plastic glove to receive the other tip.

Cinch Loop could be Isolated from Spring Arms.

An economical and effective way to create the collection bag 300 is to have one unified bag pathway 316 that contains the cinch loop of the cinch loop pull string 350 and also the first spring arm 110 and the second spring arm 120. An alternative within the scope of the present disclosure is to have one pathway for the cinch loop of the cinch loop pull string 350 which is isolated from a passageway that receives the first spring arm 110 and the second spring arm 120 (and at times the first bag interface finger 242 and the second bag interface finger 244).

Alternatives to String Channel.

The disclosure teaches the use of a string channel within the bag deployment device 100. This has some advantages as it keeps the cinch loop pull string 350 protected during the insertion of the distal end of the bag deployment device through the access cannula 400 and into the surgical cavity.

One of skill in the art will appreciate that this feature while useful is not absolutely required in order to enjoy the advantages of the teachings of the present disclosure. The cinch loop pull string 350 could run external to the outer tube 240 and perhaps run through a string channel between the outer tube and the stationary handle 210 or even external to the stationary handle 210.

Preferred Materials.

The collection bag 300 may be made of a plastic material, rip stock, or other material known to those of skill in the art that would be appropriate for the use set forth above.

The cinch loop and cinch loop pull string 350 may be made from string, suture material, mono-filament or other materials known to those of skill in the art of designing items for use in surgical techniques.

One of skill in the art will recognize that some of the alternative implementations set forth above are not universally mutually exclusive and that in some cases additional implementations can be created that employ aspects of two or more of the variations described above. Likewise, the present disclosure is not limited to the specific examples or particular embodiments provided to promote understanding of the various teachings of the present disclosure. Moreover, the scope of the claims which follow covers the range of variations, modifications, and substitutes for the components described herein as would be known to those of skill in the art.

Where methods and/or events described above indicate certain events and/or procedures occurring in a certain order, the ordering of certain events and/or procedures may be modified. Additionally, certain events and/or procedures may be performed concurrently in a parallel process when possible, as well as performed sequentially as described above.

The legal limitations of the scope of the claimed invention are set forth in the claims that follow and extend to cover their legal equivalents. Those unfamiliar with the legal tests for equivalency should consult a person registered to practice before the patent authority which granted this patent such as the United States Patent and Trademark Office or its counterpart.

What is claimed is:

1. An assembly comprising:
   a collection bag; and
   a bag deployment device;
   the collection bag comprising:
   an open end;
   a closed end opposite the open end;

the open end having a drawstring passageway with a cinch loop within the drawstring passageway;

a cinch loop pull string with a distal end that is the cinch loop around a perimeter at the open end of the collection bag and a proximal end that extends out a proximal end of the assembly; and a pair of spring openings to receive distal portions of a pair of spring arms from the bag deployment device;

the bag deployment device comprising:
a first spring arm;
a second spring arm; forming the pair of spring arms; and
each spring arm having a substantially straight proximal portion, a curved intermediate portion and a distal tip;

a drive rod comprising:
a distal end of the drive rod connected to the proximal portions of the pair of spring arms; and
a proximal end of the drive rod moved by movement of a first engagement feature; and an outer tube assembly comprising:
an outer tube that encircles a portion of the drive rod;
a stationary handle so a user can impart translation of the first engagement feature relative to the stationary handle; and
a pair of bag interface fingers located at the distal end of the outer tube adapted to engage the pair of spring openings in the collection bag as the spring arms are partially withdrawn into the outer tube; and such that the collection bag with the pair of spring openings containing the first spring arm and the second spring arm may be substantially closed by partially withdrawing the drive rod out the proximal end of the outer tube so that the pair of spring arms assumes a compressed position to substantially close the open end of the collection bag and the pair of bag interface fingers remain engaged with the pair of spring openings in the collection bag as the spring arms are partially withdrawn into the outer tube so that the collection bag is stripped from the pair of spring arms as the distal end of the bag deployment device is withdrawn into the distal end of an access cannula used for connecting an exterior of a patient with a surgical site.

2. The assembly of claim 1 wherein the assembly further comprises a string channel to receive the cinch loop pull string to protect a portion of the cinch loop pull string between distal end that is the cinch loop and the proximal end that extends out the proximal end of the assembly.

3. The assembly of claim 1 wherein the first spring arm and the second spring arm form a wishbone shape when the user imparts translation of the first engagement feature relative to the stationary handle in a distal direction.

4. The assembly of claim 1 wherein a string channel is located within an outer perimeter of the outer tube.

5. The assembly of claim 1 wherein a string channel is located within the stationary handle so the cinch loop pull string which runs external to the outer tube is routed through the stationary handle near the outer tube.

6. The assembly of claim 1 wherein the pair of spring openings to receive the pair of spring arms from the bag deployment device are open into the drawstring passageway with the cinch loop such that the pair of spring arms and the cinch loop are all in the drawstring passageway.

7. The assembly of claim 1 wherein the pair of spring openings to receive spring arms from the bag deployment device are isolated from the drawstring passageway with the cinch loop such that the pair of spring arms and the cinch loop are not all in the drawstring passageway.

8. The assembly of claim 1 wherein the first engagement feature is engaged by a thumb of a user to move the first engagement feature and the drive rod relative to the stationary handle.

9. The assembly of claim 1 wherein the drive rod is moved relative to the outer tube through use of a pistol grip trigger which is the first engagement feature that moves the proximal end of the drive rod.

10. The assembly of claim 1 wherein a distal tip of the first spring arm is adapted to interlock with a distal tip of the second spring arm in order to reduce a risk of crossover of distal tip of the first spring arm relative to the distal tip of the second spring arm.

11. The assembly of claim 1 wherein the assembly is sterilized and packaged for delivery for use in a surgical procedure.

12. A bag deployment device to deploy a collection bag with an open end and a closed end opposite the open end; the bag deployment device comprising:
a first spring arm;
a second spring arm; forming a pair of spring arms; and
each spring arm having a substantially straight proximal portion, a curved intermediate portion and a distal tip;

a drive rod comprising:
a distal end of the drive rod connected to the proximal portions of the pair of spring arms; and
a proximal end of the drive rod moved by movement of a first engagement feature; and an outer tube assembly comprising:
an outer tube that encircles a portion of the drive rod;
a stationary handle so a user can impart translation of the first engagement feature relative to the stationary handle; and
a pair of bag interface fingers located at the distal end of the outer tube adapted to engage a pair of spring openings in the collection bag as the spring arms are partially withdrawn into the outer tube; and such that the collection bag with the pair of spring openings containing the first spring arm and the second spring arm may be substantially closed by partially withdrawing the drive rod out the proximal end of the outer tube so that the pair of spring arms assumes a compressed position to substantially close the open end of the collection bag and the pair of bag interface fingers remain engaged with the pair of spring openings in the collection bag as the spring arms are partially withdrawn into the outer tube so that the collection bag is stripped from the pair of spring arms as the distal end of the bag deployment device is withdrawn into the distal end of an access cannula used for connecting an exterior of a patient with a surgical site.

13. A method of collecting an item during a surgical procedure from a surgical cavity, the method comprising:
obtaining a bag deployment device with an open end of a collection bag engaged with a pair of arms of at a distal end of the bag deployment device, the collection bag having a cinch loop pull string connected to a cinch loop around an open end of the collection bag with a proximal end of the cinch loop pull string accessible at a proximal end of the bag deployment device;

inserting a closed pair of arms at the distal end of the bag deployment device and the collection bag into a surgical cavity through an access cannula with at least a portion of the collection bag remaining external to the bag deployment device during transit of the access cannula;

opening the closed pair of arms at the distal end of the bag deployment device to open an open end of the collection bag within the surgical cavity;

inserting an item into the open end of the collection bag;

closing the pair of arms at the distal end of the bag deployment device to substantially close the open end of the collection bag within the surgical cavity;

withdrawing the closed pair of arms at the distal end of the bag deployment device from the surgical cavity while leaving the collection bag within the surgical cavity after the collection bag is stripped from a pair of bag interface fingers engaged with a pair of spring openings in the collection bag as a distal end of the bag deployment device is withdrawn into the distal end of the access cannula;

the withdrawing of the closed pair of arms pulling a proximal portion of the cinch loop pull string connected to the cinch loop around the open end of the collection bag to substantially close the open end of the collection bag as the collection bag is being stripped from the distal end of the bag deployment device by the distal end of the access cannula; and removing the collection bag from the surgical cavity to retrieve the item in the collection bag.

14. The method of claim 13 wherein inserting the closed pair of arms at the distal end of the bag deployment device and the collection bag into a surgical cavity happens without sheathing the collection bag within a deployment tube.

15. The method of claim 13 wherein the removing the collection bag from the surgical cavity to retrieve the item in the collection bag includes removing the collection bag through the access cannula.

16. The method of claim 13 wherein the removing the collection bag from the surgical cavity to retrieve the item in the collection bag includes removing the collection bag after removal of the access cannula.

17. An assembly comprising:
a collection bag; and
a bag deployment device;
the collection bag comprising:
an open end;
a closed end opposite the open end;
the open end having a drawstring passageway with a cinch loop within the drawstring passageway;
a cinch loop pull string with a distal end that is the cinch loop around a perimeter at the open end of the collection bag and a proximal end that extends out a proximal end of the assembly; and
a pair of spring openings to receive distal portions of a pair of spring arms from the bag deployment device;
the bag deployment device comprising:
a first spring arm;
a second spring arm; forming the pair of spring arms; and
each spring arm having a substantially straight proximal portion, a curved intermediate portion and a distal tip;
a drive rod comprising:
a distal end of the drive rod connected to the proximal portions of the pair of spring arms; and
a proximal end of the drive rod moved by movement of a first engagement feature; and
an outer tube assembly comprising:
an outer tube that encircles a portion of the drive rod;
a stationary handle so a user can impart translation of the first engagement feature relative to the stationary handle; and
a pair of bag interface fingers located at the distal end of the outer tube adapted to engage the pair of spring openings in the collection bag as the spring arms are partially withdrawn into the outer tube; and such that the collection bag with the pair of spring openings containing the first spring arm and the second spring arm may be substantially and reversibly closed by partially withdrawing the drive rod out the proximal end of the outer tube;

wherein
partially withdrawing the drive rod causes the pair of bag interface fingers to extend further within the pair of spring openings in the collection bag and push the pair of spring arms to assume a compressed position as the pair of spring arms are partially withdrawn into the outer tube; and the pair of spring arms substantially closes the open end of the collection bag as the pair of spring arms assumes the compressed position.

18. The assembly of claim 17 wherein the first spring arm and the second spring arm form a wishbone shape when the user imparts translation of the first engagement feature relative to the stationary handle in a distal direction.

19. The assembly of claim 17 wherein the first engagement feature is engaged by a thumb of a user to move the first engagement feature and the drive rod relative to the stationary handle.

20. The assembly of claim 17 wherein the drive rod is moved relative to the outer tube through use of a pistol grip trigger which is the first engagement feature that moves the proximal end of the drive rod.

21. The assembly of claim 17 wherein a distal tip of the first spring arm is adapted to interlock with a distal tip of the second spring arm in order to reduce a risk of crossover of distal tip of the first spring arm relative to the distal tip of the second spring arm.

22. The assembly of claim 17 wherein the assembly is sterilized and packaged for delivery for use in a surgical procedure.

23. A method of deploying a collection bag for use in collecting an item during a surgical procedure from a surgical cavity, the method comprising:
obtaining a bag deployment device with:
an open end of a collection bag engaged with a pair of spring arms of at a distal end of the bag deployment device; and
the bag deployment device having a pair of bag interface fingers that extend into a pair of spring openings in the collection bag to reversibly compress the pair of spring arms to a substantially closed position as the pair of spring arms are partially withdrawn into an opening on the bag deployment device;
substantially closing the pair of spring arms and the open end of the collection bag by partially withdrawing the pair of spring arms into the opening on the bag deployment device to cause the pair of bag interface fingers that extend into the pair of spring openings in the collection bag to reversibly compress the pair of spring arms to the substantially closed position;
inserting the closed pair of spring arms at the distal end of the bag deployment device and the collection bag into a surgical cavity through an access cannula with at least a portion of the collection bag remaining external to the bag deployment device during transit of the access cannula; and
opening the closed pair of spring arms at the distal end of the bag deployment device and the open end of the collection bag by reversing the partial withdrawal of the pair of spring arms into the opening on the bag deployment device.

24. The method of claim 23 wherein inserting the closed pair of spring arms at the distal end of the bag deployment device and the collection bag into a surgical cavity happens without sheathing the collection bag within a deployment tube.

* * * * *

UNITED STATES PATENT AND TRADEMARK OFFICE
CERTIFICATE OF CORRECTION

PATENT NO. : 10,517,579 B2
APPLICATION NO. : 16/270366
DATED : December 31, 2019
INVENTOR(S) : Andrew J. Ambro Page 1 of 1

It is certified that error appears in the above-identified patent and that said Letters Patent is hereby corrected as shown below:

Claim 13, Line 4, change 'arms of at' should read –arms at–.

Signed and Sealed this
Eighteenth Day of February, 2020

Andrei Iancu
*Director of the United States Patent and Trademark Office*